(12) United States Patent
Sokka et al.

(10) Patent No.: US 8,932,239 B2
(45) Date of Patent: Jan. 13, 2015

(54) METHOD AND APPARATUS FOR ULTRASOUND DRUG DELIVERY AND THERMAL THERAPY WITH PHASE-CONVERTIBLE FLUIDS

(75) Inventors: Shunmugavelu Sokka, Brighton, MA (US); Christopher Stephen Hall, Hopewell Junction, NY (US); Marcel Rene Bohmer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1398 days.

(21) Appl. No.: 11/914,777

(22) PCT Filed: May 25, 2006

(86) PCT No.: PCT/IB2006/051673
§ 371 (c)(1),
(2), (4) Date: Nov. 19, 2007

(87) PCT Pub. No.: WO2006/131840
PCT Pub. Date: Dec. 14, 2006

(65) Prior Publication Data
US 2008/0200845 A1 Aug. 21, 2008

Related U.S. Application Data

(60) Provisional application No. 60/688,008, filed on Jun. 7, 2005.

(51) Int. Cl.
| | |
|---|---|
| A61B 8/00 | (2006.01) |
| A61M 37/00 | (2006.01) |
| A61K 41/00 | (2006.01) |
| A61K 49/22 | (2006.01) |
| A61B 8/12 | (2006.01) |
| A61N 7/00 | (2006.01) |

(52) U.S. Cl.
CPC .............. *A61M 37/0092* (2013.01); *A61B 8/12* (2013.01); *A61N 7/00* (2013.01); *A61B 8/546* (2013.01); *A61N 7/02* (2013.01); *A61B 2017/22008* (2013.01); *A61K 41/0033* (2013.01); *A61K 49/223* (2013.01)
USPC .................................... 601/3; 601/2; 600/439

(58) Field of Classification Search
None
See application file for complete search history.

(56) References Cited

U.S. PATENT DOCUMENTS

| | | | |
|---|---|---|---|
| 5,149,319 | A | 9/1992 | Unger |
| 5,542,935 | A | 8/1996 | Unger et al. |

(Continued)

FOREIGN PATENT DOCUMENTS

| | | |
|---|---|---|
| EP | 1 723 911 A1 | 11/2006 |
| WO | 02078611 A2 | 10/2002 |

OTHER PUBLICATIONS

Sokka et al: MRI-Guided Gas Bubble, Physics in Medicine and Biology, 2003.

*Primary Examiner* — Nicholas Evoy (57) ABSTRACT

An ultrasound treatment includes applying ultrasound at a first energy level to a region of interest in a subject for activating a cavitation nucleation agent during a first portion of a treatment cycle. Ultrasound at a second energy level is applied to the region of interest during a second portion of the treatment cycle for implementing a desired thermal therapy in the presence of the cavitation nucleation agent activated during the first portion of the treatment cycle. The second energy level is at an energy level different from the first energy level.

29 Claims, 4 Drawing Sheets

(51) Int. Cl.
*A61N 7/02* (2006.01)
*A61B 17/22* (2006.01)

(56) References Cited

U.S. PATENT DOCUMENTS

| | | | |
|---|---|---|---|
| 5,657,760 A * | 8/1997 | Ying et al. | 600/439 |
| 5,762,066 A * | 6/1998 | Law et al. | 600/439 |
| 5,882,302 A * | 3/1999 | Driscoll et al. | 600/371 |
| 5,897,851 A | 4/1999 | Quay et al. | |
| 5,993,389 A * | 11/1999 | Driscoll et al. | 600/371 |
| 6,042,556 A * | 3/2000 | Beach et al. | 601/3 |
| 6,083,159 A * | 7/2000 | Driscoll et al. | 600/371 |
| 6,143,276 A * | 11/2000 | Unger | 424/9.3 |
| 6,190,315 B1 | 2/2001 | Kost | |
| 6,416,740 B1 | 7/2002 | Unger | |
| 6,569,404 B1 | 5/2003 | Quay | |
| 6,626,855 B1 * | 9/2003 | Weng et al. | 601/3 |
| 6,685,657 B2 * | 2/2004 | Jones | 601/2 |
| 2003/0009153 A1 * | 1/2003 | Brisken et al. | 604/890.1 |
| 2003/0187371 A1 * | 10/2003 | Vortman et al. | 601/3 |
| 2004/0030268 A1 * | 2/2004 | Weng et al. | 601/2 |
| 2004/0049134 A1 | 3/2004 | Tosaya et al. | |
| 2004/0059265 A1 | 3/2004 | Candy et al. | |
| 2004/0082859 A1 * | 4/2004 | Schaer | 600/459 |
| 2004/0131547 A1 | 7/2004 | Balinov et al. | |
| 2004/0162507 A1 * | 8/2004 | Govari | 601/2 |
| 2004/0265393 A1 | 12/2004 | Unger | |
| 2005/0038340 A1 * | 2/2005 | Vaezy et al. | 600/439 |
| 2005/0228318 A1 * | 10/2005 | Iger | 601/2 |
| 2007/0083120 A1 * | 4/2007 | Cain et al. | 600/439 |

* cited by examiner

METHOD AND APPARATUS FOR ULTRASOUND DRUG DELIVERY AND THERMAL THERAPY WITH PHASE-CONVERTIBLE FLUIDS

CROSS REFERENCE TO RELATED APPLICATIONS

This application claims the benefit of International Application Number PCT/IB2006/051673, filed May 25, 2006, and U.S. Provisional Application Ser. No. 60/688,008 filed Jun. 7, 2005, which are incorporated herein in whole by reference.

The present embodiments relate generally to medical ultrasound systems and more particularly, to a method and apparatus for ultrasound drug delivery and thermal therapy with phase-convertible fluids.

An important class of ultrasound contrast agents are microbubbles. Microbubbles typically contain a gas encapsulated by a protein, lipid or biodegradable polymer layer or a combination thereof. They have a typical size in the range of a few micrometers. Another class of ultrasound contrast agents is formed by liquid perfluorocarbon filled particles. Liquid perfluorocarbon filled particles are much smaller in size than microbubbles and only visible in the ultrasound field when they are accumulated.

With a trend towards targeting and drug delivery, microbubble agents have been modified to include drugs. The bubbles can be imaged and subsequently cavitated to locally release drugs, dna, or for instance, a contrast agent for another modality. A problem with the gas-filled bubbles of the microbubble agents, however, is their limited lifetime in the circulation. Accumulation at the region of interest (ROI) can take hours, while today's microbubbles persist for minutes. The breakdown pathway of these microbubbles is not always clear, but it can be anticipated that it may lead to release of drugs slowly at undesired locations. Accordingly, there exists a need for a more stable ultrasound assisted drug delivery strategy. Yet another problem with microbubbles is that they remain in the vasculature and therefore drug delivery can only take place in or from the vasculature.

In addition to the above, ultrasound has been used for inducing cavitation in tissue. The known methods required very high pressures to exceed the cavitation threshold in tissue, which puts significant demands on the ultrasound transducer and power electronics.

Furthermore, numerous studies have shown the benefits of cavitation-enhanced heating when ablating tissues with high intensity focused ultrasound. By this mechanism of cavitation-enhanced heating, microbubbles created at the focus during heating exposures enhance local absorption and thereby increase the heat deposition at the focal point. Ultrasound heating in the presence of bubbles produces larger lesions at lower therapeutic powers than ultrasound heating without bubbles. As result of this phenomenon, researchers have also investigated ultrasound heating in the presence of vascularly introduced microbubble contrast agents and have shown enhanced heating significantly reduces the power requirements on the therapy transducer. However, the presence of microbubbles in all regions of tissue can interfere with the propagation of the therapy beam and also increases the likelihood of off-focal cavitation and heating.

Focused ultrasound (FUS) therapy has been investigated to thermally coagulate pathological tissue in the treatment of benign and cancerous tumors in several organs systems. Although focused ultrasound therapy can induce cavitation to mechanically destroy tissue, the dominant opinion in the ultrasound therapy community has been to avoid cavitation and induce more predictable and controllable thermal damage with focused ultrasound. In most focused ultrasound therapies, heating is used for treatment. With such treatment, thermal bioeffects are better characterized and controlled, yielding lesion sizes and shapes predicted by various models. For example, FUS thermal ablation is performed with constant levels of ultrasound intensity, below the cavitation threshold, for durations of 1-30 seconds to raise the temperature at the focus to levels that denature protein. In addition, therapy in the thermal regime can be carefully monitored with thermometry techniques, most notably magnetic resonance imaging (MRI).

However, much has been learned about cavitation since the early in vivo cavitation studies. High Intensity focused ultrasound-generated gas bubbles of introduced microbubble contrast agents have some potentially useful properties during focused ultrasound therapy. Besides generating extremely high temperatures and concentrating acoustic energy at the cavitation site, theoretical models, extracorporeal, ex vivo, in vitro, and phantom experimental work have shown that gas bubbles in a focused ultrasound field yield higher ultrasound absorption and therefore higher bulk temperatures in a zone near the focus. Higher temperatures yield higher thermal doses at the focus, so this gas bubble enhanced heating method could lead to more efficient FUS treatment protocols. In vivo studies have shown that occasional cavitation and/or boiling during these thermal mode exposures can enhance the heating effect. When cavitation is detected, atypical lesion sizes and shapes result. These results show the promise as well as the unpredictability of cavitation-enhanced heating. In all of these studies, the induction and timing of cavitation was unpredictable, and thus the overall enhanced heating effect was neither predictable nor controllable.

More recent work has shown that if gas bubbles and cavitation are induced at the proper time and the proper place during bubble-enhanced heating exposure, predictable and more uniform lesions can be generated. This work showed that for equal energy level exposures, a therapeutic ultrasound exposure in the presence of gas bubbles at the onset of heating reliably produces on average lesions three times larger in volume than therapeutic exposures without bubbles.

Accordingly, an improved method and ultrasound therapy treatment system for overcoming the problems in the art is desired.

According to an embodiment of the present disclosure, an ultrasound treatment includes applying ultrasound at a first energy level to a region of interest in a subject for activating a cavitation nucleation agent during a first portion of a treatment cycle. Ultrasound at a second energy level is applied to the region of interest during a second portion of the treatment cycle for implementing a desired thermal therapy in the presence of the cavitation nucleation agent activated during the first portion of the treatment cycle. The second energy level is at an energy level different from the first energy level. The method can be implemented by an ultrasound therapy treatment system, as well as in the form of a computer program product.

FIG. 4 contains pictoral views of (a) an MRI view showing a region of tissue with focus of a conventional therapeutic ultrasound heating exposure (no gas bubbles), (b) an MRI showing a region where heating is to occur, with bone just above a focal location, during gas-bubble enhanced heating according to an embodiment of the present disclosure, (c) an MRI temperature image showing heating as ultrasound reflects off the bone of the image of FIG. 4(a) above the focal point, and (d) an MRI temperature image during a gas-bubble enhanced heating, post conversion of a corresponding phase-convertible agent, showing no heating above the focal point where the bone of FIG. 4(b) might reflect energy, but does not, in view of the method according to the embodiments of the present disclosure.

In the figures, like reference numerals refer to like elements. In addition, it is to be noted that the figures may not be drawn to scale.

According to one embodiment of the present disclosure, enhanced heating is accomplished with the use of phase-convertible agents. Phase-convertible agents, such as, perfluorocarbon-based solutions and emulsions can be safely injected into the blood stream. At normal body temperatures, these agents are in the liquid phase and can be synthesized with their boiling points lower than that of water.

According to another embodiment, the method comprises using high intensity focused ultrasound to focally raise the acoustic pressure and/or temperature at a desired location. The method includes phase converting the phase-convertible agents to the gas phase and using the phase converted agents in the gas phase to enhance heating and heat-related biological effects. The phase-convertible agents could also be targeted to the sites of pathology, further localizing the focused ultrasound therapy. In addition, an ultrasound shielding effect of gas bubble layers could be used to protect critical anatomy during focused ultrasound therapy. Furthermore, heating-based focused ultrasound therapies in the presence of nanoparticles will ultimately reduce transducer power requirements, allow for the heating of larger areas, and better localize ultrasound energy deposition.

Accordingly, the methods of therapeutic ultrasound with phase-convertible fluids according to the embodiments of the present disclosure overcome both the power disadvantages of inducing cavitation in tissue and the poor spatial control when heating in the presence of injected microbubble contrast agents.

Figure 1:
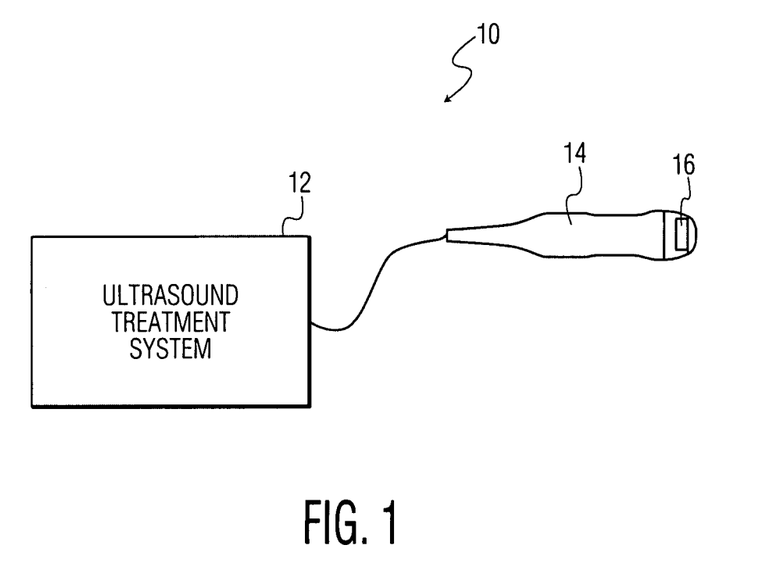
FIG. 1 is a partial block diagram view of an ultrasound therapy treatment system according to an embodiment of the present disclosure.

Referring now to the drawings, FIG. 1 is a block diagram view of an ultrasound therapy treatment system 10 according to an embodiment of the present disclosure. The ultrasound therapy treatment system 10 includes a control or base unit 12 configured for use with an ultrasound transducer probe 14, further for carrying out the ultrasound treatment methods as discussed herein according to the embodiments of the present disclosure. The probe 14 contains an ultrasound transducer 16.

In one embodiment, ultrasound transducer 16 comprises a high power ultrasound transducer. In addition, transducer 16 can comprise a single element or a phased array, wherein the choice between that of the single element or phased array is selected according to the requirements of a particular ultrasound treatment application. Furthermore, base unit 12 includes suitable control electronics for performing ultrasound therapy treatment as discussed herein. For example, in one embodiment, base unit 12 can comprise a computer as discussed further herein. Ultrasound transducer probe 14 couples to base unit 12 via a suitable connection, for example, an electronic cable, a wireless connection, or other suitable means.

Figure 2:
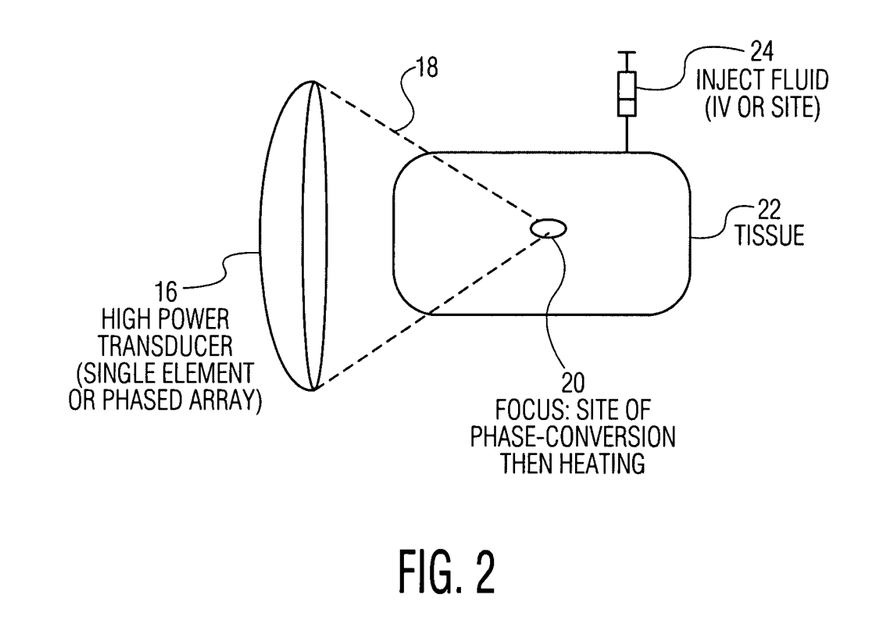
FIG. 2 is a simplified schematic diagram view of therapeutic treatment of a target location with use of the ultrasound therapy treatment system according to an embodiment of the present disclosure.

FIG. 2 is a simplified schematic diagram view of ultrasound therapy treatment of a target location with use of the ultrasound treatment system 10 according to an embodiment of the present disclosure. In particular, ultrasound transducer 16 produces ultrasound energy 18 that is focused at a target location 20 in response to an activation signal from base unit 12. The focal point of the ultrasound energy can be adjusted as needed, for example by a repositioning of the probe 14 with respect to the target location 20 and/or through appropriate activation signals from base unit 12, according to the requirements of a particular ultrasound treatment application. Target location 20 is disposed in a region of interest within tissue 22 of a subject to be treated according to the methods of the present disclosure. For example, tissue 22 may comprise any tissue within a human body or within an animal body. In addition, one or more contrast agents according to the embodiments of the present disclosure can be administered by injecting fluid using an intravenous (IV) or a site injection, as indicated by reference numeral 24. In one embodiment, the intravenous can be administered distal from the region of interest, whereas, the injection can be administered proximate the region of interest.

Figure 3:
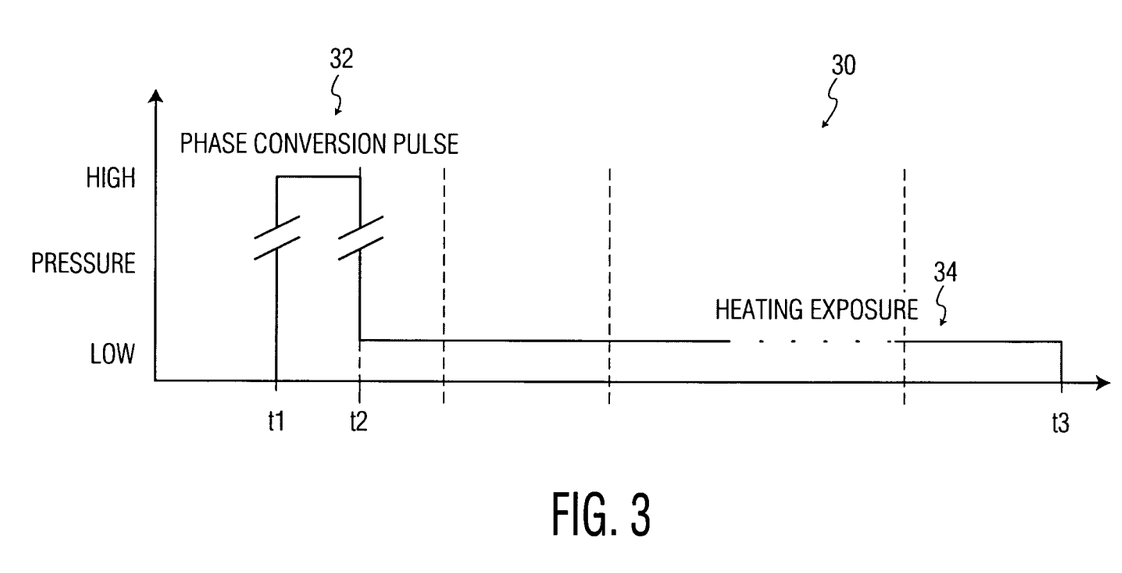
FIG. 3 is an exemplary timing diagram illustrating ultrasound therapy pressure versus time according to one embodiment of the present disclosure.
Figure 4A:
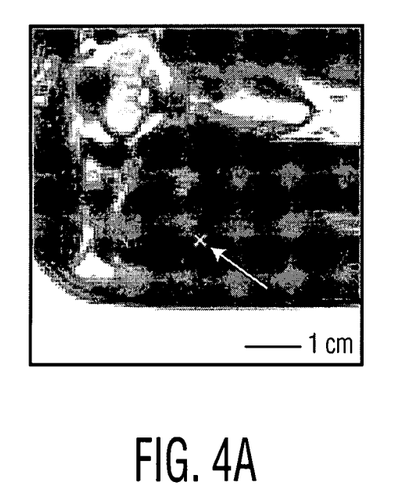
Figure 4B:
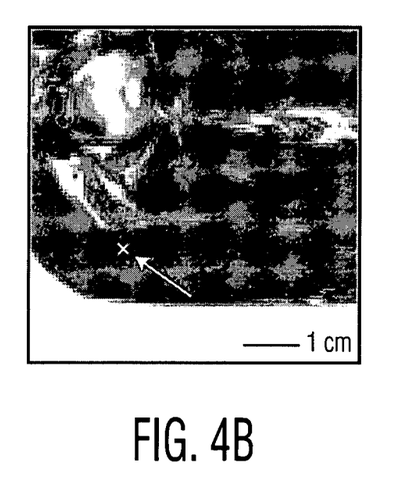
Figure 4C:
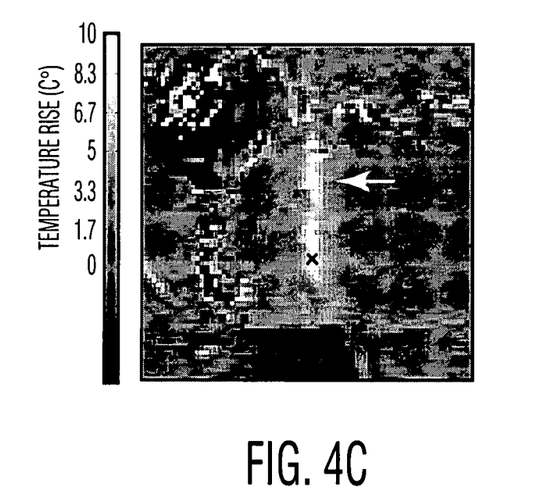
Figure 4D:
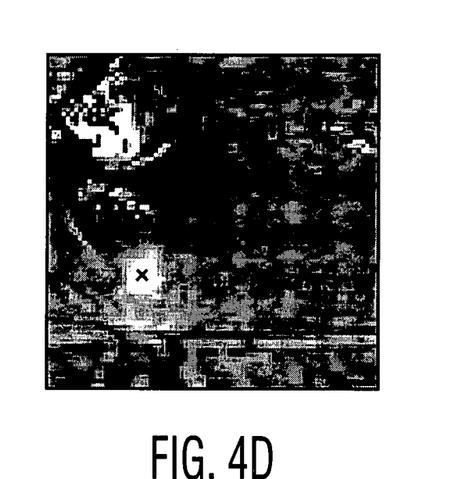

FIG. 3 is an exemplary timing diagram illustrating ultrasound therapy pressure versus time according to one embodiment of the present disclosure. An initial high pressure, short duration phase conversion pulse 32 is used to focally create gas bubbles in response to phase-conversion of the nucleation cavitation agent. Pulse 34 comprises an immediately following heating exposure that makes use of the focally created gas bubbles to provide a gas-bubble enhanced heating exposure, the gas-bubble enhanced heating exposure providing a desired treatment to tissue 22 at the target location 20. In one embodiment, the first pulse 32 corresponds to a first phase and the second pulse 34 corresponds to a second phase. During the second phase, there can occur an absence of cavitation, for example, as a result of no more nuclei present or lower pressures/different frequencies provided by the transducer. In another embodiment, pulse 32 occurs between times t1 and t2 and pulse 34 occurs between times t2 and t3. Activation of the transducer 16 produces pulse 32, 34, and any other pulses, in response to appropriate activation signals from base unit 12. For example, the transducer 16 could be activated with use of an intermittent pulsing scheme to allow for reperfusion. The intermittent pulsing scheme could include a first pulse for phase conversion, a second pulse for heating, an off period or period of no pulse to allow for new particles to flow into the treatment plane, and then repeating the intermittent pulsing scheme with the first pulse, the second pulse, and the off period of no pulse, for as many repetitions as may be desired for a given treatment plan.

FIG. 4 contains pictoral views of various images as discussed in the following. In FIG. 4(a), an MRI view shows a region of rabbit tissue with an X indicating the focus of a conventional therapeutic ultrasound heating exposure with no gas bubbles. Above and to the left of the focus in FIG. 4(a) are bone structures, the bone structures appearing white. In FIG. 4(b), an MRI view shows a region where heating is to occur with bone just above a focal location, during gas-bubble enhanced heating according to an embodiment of the present disclosure. In FIG. 4(c), an MRI temperature image shows heating above the focal point as ultrasound reflects off the bone of the image of FIG. 4(a). Additionally, FIG. 4(d) shows an MRI temperature image captured during a gas-bubble enhanced heating, post conversion of a corresponding phase-convertible agent. As can be observed in FIG. 4(d), the image shows no heating above the focal point where the bone of FIG. 4(b) might reflect energy, but does not, in view of the method according to the present embodiments. In FIG. 4(d), the gas-bubble is created by cavitation via a very high-pressure pulse, for example, pulse 32 of FIG. 3.

According to one embodiment of the present disclosure, the method of gas-bubble enhanced ultrasound heating includes the use of biological safe, injectable phase-convertible fluids to gain the benefit of reducing therapeutic power requirements while maintaining tight spatial control of the ultrasound heating. Furthermore, the method provides benefits as outlined herein above.

In another embodiment, the method includes choosing a material configured to enhance the production of gas at the focus of a therapeutic ultrasonic transducer. The criteria for a correct choice of material involves the selection of a bulk material to be phase converted, a method of delivery (particle-like or homogeneous solution), characteristics of the delivery mechanism, and an appropriate concentration. An important aspect of the method, and corresponding design of such a system, is that the bulk material (or corresponding particles) be in a non-gaseous state at body temperature. In the method, the introduction of prescribed focused ultrasound energy instigates a phase change in the bulk material from solid/liquid to gas.

The method further comprises use of perfluorocarbon-filled nanoparticles/microparticles that are in the liquid state at body temperature. The perfluorocarbon includes perfluorocarbon having a boiling point in a temperature range that is attainable through the introduction of focused ultrasound. In addition, the perfluorocarbon-filled nanoparticles/microparticles can comprise encapsulated particles or free droplets. Furthermore, the particular encapsulation is one selected to help control the onset of cavitation. For example, common methods of encapsulation are through lipid layers and polymer shells. Still further, the choice of the size of the particles will depend on the application, with particles of appropriate size being chosen for their accessibility to a targeted vasculature, as well as to the size of the particles post-phase conversion.

While the embodiments of the present disclosure have been disclosed as using nanoparticles or microparticles, the embodiments of the present disclosure can also include the use of homogeneous solution as might occur, for example, in blood substitutes. One of the common methods of providing a blood substitute is to use a perfluorocarbon liquid. In addition, any or all of these agents may be coupled to an agent that binds to a specific target in the body. For example, the agent may include an antibody to AlphaV-Beta3 integrin, which binds to areas of neo-vasculature as found in a tumor. By introducing an injection of the solution or fluid, one might also expect to cavitate or phase-convert this liquid with the use of focused ultrasound.

In addition to the enhanced heating effect, the phased converted gas bubbles obtained via post conversion of a corresponding phase-convertible agent and provided by the various embodiments of the method of the present disclosure will have ultrasound-shielding effects. That is, the phase converted gas bubbles could also be used to protect tissues or vital anatomy beyond a gas layer during focused ultrasound therapy. Accordingly, the method further comprises creating shielding layers during therapy by phase-converting the fluid at the focus. In other words, the method includes ablating tissue at the ultrasound focus and protecting tissue beyond the ultrasound focus (FIG. 4).

In another embodiment, the phase-convertible liquid agent is injected intravascularly. Alternatively, the phase-convertible liquid agent can be injected in the vicinity of the treatment zone. Subsequent to the injection of the phase-convertible liquid agent, focused ultrasound of sufficient energy is used to phase-convert the liquid into gas at the desired treatment location (FIG. 2). Immediately following conversion, lower-pressure heating exposures focused at or below the phase-conversion focus are used to ablate or heat the treatment region in the presence of the phase-converted gas bubbles. FIG. 3 illustrates one example of a complete ultrasound exposure profile.

In such an embodiment, lower pressures than would be required to cavitate tissue in an absence of microbubbles are needed to phase-convert the injected liquid/emulsion, thereby reducing the therapy system energy requirements. In addition, the initial phase conversion will be used to shield structures in a region beyond the therapeutic focus.

In another embodiment, targeted phase-convertible liquid agent is injected intravascularly or in the vicinity of the treatment zone. After a period of time required for binding of the agent to the target location, focused ultrasound of sufficient energy is used to phase-convert the liquid into gas at the desired treatment location. Immediately following conversion, lower-pressure heating exposures focused at or below the phase-conversion focus are used to ablate or heat the treatment region in the presence of the phase-converted gas bubbles. FIG. 3 illustrates one example of a complete ultrasound exposure profile. In such an embodiment, targeting is used to increase the amount of fixed phase-convertible agent at the desired treatment so that less power maybe required during both the phase-conversion and heating time periods. In addition, the initial phase conversion will be used to shield structures in a region beyond the therapeutic focus.

In another embodiment, the phase-convertible liquid agent is injected intravascularly or in the vicinity of the treatment zone. Focused ultrasound of sufficient energy is used to phase-convert the liquid into gas at the desired shielding location or locations. In such an instance, the phase-convertible liquid is selected so as to provide gas that can remain in the gas phase for a desired time duration at the shielding location or locations, subsequent to conversion of the liquid into gas. Then, focused ultrasound of sufficient energy is used to phase-convert the liquid into gas at the desired treatment location. The phase-convertible liquid is also selected so as to provide gas that can remain in the gas phase for a desired time duration at the treatment location, subsequent to conversion of the liquid into gas. Immediately following conversion, lower-pressure heating exposures focused at or below the phase-conversion focus are used to ablate or heat the treatment region in the presence of the phase-converted gas. In such an embodiment, shielding may be applied at a prescribed distance from the treatment zone. In other words, shielding proximate the treatment location provides protection of distal regions from heating effects originating at the treatment location. Such heating effects originating at the treatment location may be undesirable at the distal region or regions. The protected distal region corresponds to a region located on an opposite side of the shielding locations away from the treatment location.

The embodiments described herein can be used in any application in which focused ultrasound is used to thermally ablate tissue. The embodiments can also be used in any applications where low temperature heating is desired for a bioeffect. For example, the applications may include, but are not limited to, FDA approved HIFU devices for ablation of abdominal tumors, thermally activated gene therapy, thermally induced drug delivery, HIFU devices approved in Europe for prostate cancer, and future applications for treating brain tumors. By essentially improving the heating efficiency, the method according to the embodiments of the present disclosure would reduce transducer and driving system power requirements and complexity such that ultrasound-heating therapy might be possible with unfocused transducers similar to conventional imaging transducers geometries. In addition, intracavitary application can be improved as transducer size-related power limitations may be overcome.

As discussed herein, focused ultrasound can be used to deposit energy at a region of interest. Using this energy, phase conversion of a liquid into a gas can be established at the ROI. If the liquid, such as a fluorinated liquid with a relatively low boiling point, but a boiling point above 37° C., is encapsulated in a shell, such as a shell of a biodegradable polymer, the shell will break up, gas escapes, and drug delivery or effective thermal treatment can take place. Compared to bubbles that have a gaseous core at body temperature, these particles have a much better lifetime in the circulation. Compared to known phase shift "emulsions" the liquids used in the embodiments of the present disclosure have the advantage that they will become liquid again after cooling down to body temperature, avoiding the formation of large gas bubbles in the circulation.

Using a phase conversion mechanism, much smaller particles can be used and that can still be visualized clearly using ultrasound once they convert from liquid to gas. By using (slowly) biodegradable shells, drug release when not activated is minimized. By analogy to the liquid perfluoro-carbon containing agents described in the introduction, once accumulated, the particles can be visualized using ultrasound (or F-nmr) without damaging them. Subsequently using a higher intensity, the phase conversion and concomitant drug release can take place, which can be followed with diagnostic ultrasound.

Phase Conversion:

For local drug delivery, it is desirable to have an agent that has a phase conversion above body temperature and below the boiling point of water. Perfluorocarbons have, compared to corresponding alkanes, relatively low boiling points. For example, perfluoro-octane has a boiling point of 99° C. and per-fluoro heptane has a boiling point of 80° C. If the heat of evaporation is low compared to that of water, cavitation can be achieved using ultrasound, especially with therapeutic ultrasound transducers. Having a boiling point above body temperature also leads to condensation once the ultrasound is stopped and the temperature in the ROI decreases again. As a result, the risk of formation of uncontrollable large gas bubbles is therefore minimized.

Imaging:

Perfluorocarbon containing nanoparticles have been imaged by Wickline, when accumulated on fibrin. Contrary to microbubbles, perfluorocarbon containing nanoparticles could not be detected when flowing in the vasculature. These particles have a broad size distribution with a mean diameter of 250 nm. To allow for sufficient drug incorporation, according to one embodiment of the present disclosure, the method includes using bigger particles, thereby making imaging easier. Alternatively, the perfluorocarbon containing nanoparticles can be imaged using Fluor MRI.

Upon phase conversion, gas bubbles appear that give a high acoustic signal and that can be imaged using suitable measuring techniques, for instance detecting harmonics or using phase inversion.

Thermal Therapy:

Cavitation or the presence of phase-converted gas bubbles increases dramatically the local tissue absorption at the site of the gas bubbles. Accordingly, the first pulse of the therapy beam is used to phase convert, then CW (continuous wave) ultrasound is used to heat at the desired treatment area. From studies, it has been shown that up to three (3) times larger lesions for equivalent ultrasound power when microbubbles are present can be achieved at the thermal focus. Accordingly, ultrasound power can be dropped and similar lesion size obtained when phase-converted microbubbles from the phase-convertible liquid are present. Another significant advantage of phase-converted microbubbles from the phase-convertible liquid at the focus region when thermal heating is initiated is that temperature rise occurs much faster. That is, temperature rise occurs in a step function fashion rather than a typical logarithmic heating fashion. This might be useful in applications for thermal activation where a quicker temperature rise is needed. If liquid perfluorocarbon is used instead of bubbles, then bubble lifetime issues are solved while, if the particles are adhered, imaging of accumulated particles is still possible before cavitation is induced.

Particle Preparation:

Liquid perfluorocarbon containing particles can be prepared using emulsion methods. The shell forming material, for instance biodegradable polymers such as polylactic acid, poly glycolic acid, polycaprolacton mixtures or copolymers thereof are dissolved in a suitable solvent. The perfluorocarbon is added and mixed well into the polymer solution. Subsequently, an emulsion in water is made by pouring the fluorocarbon containing polymer solution in an aqueous solution. The aqueous solution may contain a stabilizer, an often used stabilizer is poly vinyl alcohol. The emulsion can be processed to obtain the desired size distribution by standard emulsification and filtration methods.

Instead of a stabilizer added to the aqueous phase, a block copolymer having a hydrophilic block can be used as one of the polymers employed to make the shell of the particles. A common choice for this hydrophilic block is poly ethylene oxide, which has the advantage that it delays the uptake of the particle by the RES. In addition, a pegylated chain can be used as a starting point for the synthesis of a targeted agent. To optimize the size control, drop-by-drop emulsification methods such those using cross-flow filtration, liquid jets are preferred.

Further in continuation of the preparation procedure, the solvent for the polymer has to be removed. Often a solvent is chosen that has a fairly low boiling point or a reasonable solubility is the aqueous phase. As a consequence, the emulsion droplets will shrink. As the polymer will become insoluble upon removal of the solvent, it will form a shell and the remaining liquid will form the core of the particle.

Drug Incorporation:

Drugs are most effective when they are dissolved in a suitable solvent. A distinction has to be made between lipophilic and hydrophilic drugs. Lipophilic drugs can be incorporated using the emulsification procedure described above. A solution of the drug in oil with a very high boiling point (the oil should not be cavitated) can be added to the polymer solution. At sufficiently low initial concentrations, this does not affect the solubility of the polymer. An example of a drug that can be incorporated using this route is paclitaxel.

Hydrophilic drugs or dna require a different preparation procedure. Here double emulsion techniques have to be used. A small amount water containing the drug or the dna is emulsified with the polymer solution and the perfluororcarbon. This first emulsion is subsequently poured into an aqueous phase not containing the drug, as is known for a double emulsion preparation of a cavitation nucleation agent. An interesting hydrophilic drug is adenosine that is used in making stress echo's.

EXAMPLES

1) Preparation of Perfluoro-Oactane Filled Poly-Lactic co Glycolic Acid Particles 0.24 g of a 5% plga solution in dichloromethane was added to 0.12 g of perfluoro-octane. 0.8 grams of additional dichloromethane was added. The mixture was poured into a 0.3% pva (8/88) solution in water, shaken for 1 minute and filtered ten times over an acrodisk glass filter. The samples were left to evaporate of the DCM overnight under mild agitation. The next day the sample were centrifuged three times and resuspended in water to remove excess pva and lipid not containing pfo. The PFO concentration was measured using F-nmr using pentadecafluorooctanoic acid as a reference. The concentration was 56 mM. The particle size was determined with dynamic light scattering using a Coulter n4plus. Measurements took place at 90 degrees and were fitted using the cumulant method. The average particle diameter found was 940 nm with a standard deviation of 280 nm.

2) Ultrasound Measurements

The particles as described in example 1 were injected (0.5 ml) in circulating degassed water and the flow was stopped when the particles had filled up the cell. The cell was equipped with 6 micrometer mylar foil for XRF (3517 MYLAR) acoustically transparent windows and immersed in a water tank. A 2.7 MHz therapy transducer with a focal length of 2.5 cm was placed such that the focus was in the middle of the cell. At a setting of near 1 MPa clear formation of phase-converted liquid generated gas bubbles took place as detected using a 12 MHz linear array transducer with 5 MHz bandwidth using a HDI5000 system in regular imaging mode. In a control measurement, no cavitation could be observed up to at least 1.25 MPa.

3) Preparation of Perfluoro-oactane Filled Poly-Lactic co Glycolic Acid Particles 0.21 g of a 5% plga solution in dichloromethane was added to 0.25 g of perfluoro-octane. 0.6 grams of additional dichloromethane was added. The mixture was poured into a 0.3% pva (8/88) solution in water, shaken for 1 minute and filtered ten times over an acrodisk glass filter. The samples were left to evaporate of the DCM overnight under mild agitation. The next day the sample were centrifuged three times and resuspended in water to remove excess pva and lipid not containing pfo. The PFO concentration was measured using F-nmr using pentadecafluorooctanoic acid as a reference. The concentration was 65 mM. The particle size was determined with dynamic light scattering using a Coulter n4plus. Measurements took place at 90 degrees and were fitted using the cumulant method. The average particle diameter found was 910 nm with a standard deviation of 280 nm.

4) Ultrasound Measurements

The particles as described in example 3 were injected (0.5 ml) in circulating degassed water and circulated until well mixed with the water. The cell was equipped with 6 micrometer mylar foil for XRF (3517 MYLAR) acoustically transparent windows and immersed in a water tank. A 2.7 MHz therapy transducer with a focal length of 2.5 cm was placed such that the focus was in the middle of the cell. At a setting of 1 MPa clear formation of phase-converted liquid generated gas bubbles took place as detected using a 12 MHz linear array transducer with 5 MHz bandwidth using a HDI5000 system in regular imaging mode. In a control measurement no cavitation could be observed up to at least 1.25 MPa.

In addition to the above, the embodiments of the present disclosure also include computer software or a computer program product. The computer program product includes a computer readable media having a set of instructions for carrying out the method of the ultrasound treatment as described and discussed herein. The computer readable media can include any suitable computer readable media for a given ultrasound diagnostic/therapeutic imaging system application. Still further, the computer readable media may include a network communication media. Examples of network communication media include, for example, an intranet, the Internet, or an extranet.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can also be applied to any phase-convertible nucleation cavitation agent having a boiling point above 100 degrees C. Such an instance might be useful if the system locally lowers the pressure with ultrasound thereby affecting the corresponding agent's published boiling point. Furthermore, locally in a focused region of interest, the system can heat the region of interest to above 100 degrees C. for the phase conversion. Furthermore, embodiments of the present disclosure may also be used in non-intra-venous manners, for example, via intra-mascular or even intracavity (such as, in the uterus) where larger particles for the phase-convertible neucleation cavitation agents can be used. In such an instance, the particle size can be greater than 10 microns. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A method of ultrasound treatment comprising the acts of:
applying first ultrasound at a first energy level to a shielding location outside a region of interest in a subject for activating a cavitation nucleation agent at the shielding location during a first portion of a treatment cycle, wherein the activated cavitation nucleation agent creates a shielding layer at the shielding location to shield structures outside the region of interest;

after the act of applying the first ultrasound, applying second ultrasound at a second energy level to a treatment location inside the region of interest for activating the cavitation nucleation agent at the treatment location inside the region of interest during the first portion of the treatment cycle; and immediately after the act of applying second ultrasound at the second energy level, applying third ultrasound at a third energy level to the treatment location inside the region of interest during a second portion of the treatment cycle for implementing a desired thermal therapy in the presence of the cavitation nucleation agent activated during the first portion of the treatment cycle, wherein the third energy level is at an energy level different from the second energy level.

2. The method of claim 1, further wherein the cavitation nucleation agent comprises a phase-convertible fluid and wherein the first portion includes phase conversion of the phase-convertible fluid.

3. The method of claim 2, further wherein the phase-convertible fluid includes a liquid having a boiling point above 37 degrees Celsius and below 100 degrees Celsius.

4. The method of claim 3, further wherein the liquid contains particles.

5. The method of claim 4, further wherein the particles comprise liquid perfluorocarbon filled particles below 37 degrees Celsius.

6. The method of claim 4, further wherein the particles have a size less than or equal to 5 microns.

7. The method of claim 4, further wherein the particles are encapsulated with a biodegradable polymer shell.

8. The method of claim 1, wherein a drug is delivered during the first portion.

9. The method of claim 8, wherein the cavitation nucleation agent comprises a phase-convertible fluid and wherein the first portion includes phase conversion of the phase-convertible fluid.

10. The method of claim 1, wherein a continuous wave ultrasound is applied during the second portion for providing an ultrasound thermal treatment.

11. The method of claim 10, wherein the ultrasound thermal treatment includes thermal therapy for inducing thermal damage in the region of interest.

12. The method of claim 1, wherein the first and second energy levels are sufficient for enabling ultrasound induced phase conversion of a phase-convertible fluid.

13. The method of claim 12, further wherein the phase-convertible fluid includes a liquid having a boiling point above 37 degrees Celsius and below 100 degrees Celsius.

14. The method of claim 13, further wherein the liquid contains particles.

15. The method of claim 14, further wherein the particles comprise liquid perfluorocarbon filled particles.

16. The method of claim 14, further wherein the particles have a size less than or equal to 5 microns.

17. The method of claim 14, further wherein the particles are encapsulated with a biodegradable polymer shell.

18. The method of claim 1, wherein the first and second energy levels are sufficient for activating the cavitation nucleation agent and wherein the third energy level is insufficient for activating the cavitation nucleation agent.

19. The method of claim 1, wherein the first, second, and third energy levels are insufficient to activate the cavitation nucleation agent for mechanically destroying tissue in the region of interest.

20. The method of claim 10, wherein an ultrasound induced phase conversion and an ultrasound thermal treatment occur within the shielding and treatment locations alone.

21. The method of claim 20, wherein the ultrasound thermal treatment includes bubble-enhanced heating.

22. The method of claim 1, wherein the first ultrasound at the first energy level, the second ultrasound at the second energy level and the third ultrasound at the third energy level comprise focused ultrasound and wherein the ultrasound treatment comprises focused ultrasound therapy.

23. The method of claim 22, wherein the third ultrasound at the third energy level is used for focused ultrasound thermal ablation.

24. The method of claim 23, wherein the third energy level is at or above a level sufficient for thermal ablation, but below a cavitation threshold of tissue in the region of interest.

25. The method of claim 22, wherein the activated cavitation nucleation agent is activated a focused ultrasound for the focused ultrasound therapy.

26. The method of claim 1, wherein the first ultrasound at the first energy level, the second ultrasound at the second energy level and the third ultrasound at the third energy level comprise focused ultrasound, and further wherein responsive to (i) a presence of a phase-convertible fluid and (ii) application of focused ultrasound at the first energy level, the phase-convertible fluid and the focused ultrasound generate gas-bubbles in the region of interest.

27. The method of claim 1, further comprising the act of:
delivering a phase-convertible fluid to the region of interest, wherein the act of delivering includes one of intravenous delivery at a first location far from the region of interest and injection delivery at a second location nearer to the region of interest than the first location.

28. An ultrasound apparatus comprising:
a computer;
an ultrasound probe; and
an ultrasound transducer disposed within the ultrasound probe and coupled to the computer, wherein said computer is configured for controlling the ultrasound transducer in an ultrasound treatment comprising the acts of:
applying first ultrasound at a first energy level to a shielding location outside a region of interest in a subject for activating a cavitation nucleation agent at the shielding location during a first portion of a treatment cycle, wherein the activated cavitation nucleation agent creates a shielding layer at the shielding location to shield structures outside the region of interest;
after the act of applying the first ultrasound, applying second ultrasound at a second energy level to a treatment location inside the region of interest for activating the cavitation nucleation agent at the treatment location inside the region of interest during the first portion of the treatment cycle; and
immediately after the act of applying second ultrasound at the second energy level, applying third ultrasound at a third energy level to the treatment location inside the region of interest during a second portion of the treatment cycle for implementing a desired thermal therapy in the presence of the cavitation nucleation agent activated during the first portion of the treatment cycle, wherein the third energy level is at an energy level different from the first energy level.

29. The method of claim 1, wherein the second ultrasound consists of a single pulse having an amplitude which is higher than an amplitude of the third ultrasound and a duration which is less than a duration of the third ultrasound.

* * * * *